United States Patent [19]

Andrews

[11] Patent Number: 5,154,724
[45] Date of Patent: Oct. 13, 1992

[54] ATHERECTOMY CATHETER

[76] Inventor: Winston A. Andrews, 5583 Paseo Navarro, Pleasanton, Calif. 94566

[21] Appl. No.: 826,258

[22] Filed: Jan. 24, 1992

Related U.S. Application Data

[63] Continuation of Ser. No. 523,216, May 14, 1990, abandoned.

[51] Int. Cl.⁵ .............................................. A61B 17/32
[52] U.S. Cl. ......................................... 606/159; 604/22
[58] Field of Search .................... 128/751; 604/22; 606/159, 170, 180

[56] References Cited

U.S. PATENT DOCUMENTS

| | | | |
|---|---|---|---|
| 4,445,509 | 5/1984 | Auth | 128/752 X |
| 4,885,003 | 12/1989 | Hillstead | 604/22 |
| 4,886,061 | 12/1989 | Fischell et al. | 604/22 X |
| 4,895,560 | 1/1990 | Papantonakos | 606/159 X |
| 4,966,604 | 10/1990 | Reiss | 606/159 |
| 5,000,185 | 3/1991 | Yock | |
| 5,030,201 | 7/1991 | Palestraut | 604/22 |

*Primary Examiner*—Michael H. Thaler
*Attorney, Agent, or Firm*—Lyon & Lyon

[57] ABSTRACT

An atherectomy catheter including an expandable cutter head having spaced apart blades radially extending from a cutter sleeve at a leading end of the cutter head. A torque tube is attached to and surrounds the blades at an expanding end of the cutter head opposite the leading end. An expander cable is attached to a bushing within the cutter head adjacent to the cutter sleeve and blades with the expander tube axially displaceable through the torque tube. A guidewire slidably extends through the bushing and expander tube. A guiding catheter substantially encloses the torque tube with the toruqe tube rotatable and axially displaceable within the guiding catheter, to rotate the cutter head as it engages a blockage in a blood vessel.

9 Claims, 3 Drawing Sheets

ATHERECTOMY CATHETER

This is a continuation of co-pending application Ser. No. 07/523,216, filed on May 14, 1990, now abandoned, and which designated the U.S.

BACKGROUND OF THE INVENTION

Athersclerosis is a disease of the circulatory system characterized by fatty or calcified deposits or fibrous tissue growth which occlude blood vessels. It is a leading cause of death by disease in the United States. The atheroesclerotic stenoses or blockages tend to reduce cross sectional area of the blood vessels thereby impeding blood circulation. In severe cases, the entire vessel may be significantly narrowed or blocked by the deposits, thereby causing or contributing angina pectoris, stroke, myocardial infarction and other conditions.

Athersclerosis may be treated through coronary by-pass surgery wherein an autogenous vein or synthetic graft is used to by-pass the diseased artery. Of course, this technique involves a major surgical operation at substantial risk and expense to the patient, and a significant recovery period.

Balloon angioplasty is another method for treating athersclerosis. With this technique a balloon catheter is routed through the artery to the site of the blockage. Once in position, the balloon is inflated to compress or displace the blockage. Balloon angioplasty requires only local anesthesia and avoids many of the risks, expenses and prolonged recovery associated with by-pass surgery. However, if the blockage or stenosis is asymmetrical or fully closed, this technique may be unavailable or ineffective. Similarly, balloon angioplasty may not work with highly calcified or fibrous blockages.

Various atherectomy catheters having mechanical cutting edges for cutting blockages have also been proposed. While these devices have met with varying degrees of success in principle and application, certain disadvantages remain. If a single cutting device is unable to remove a wide range of blockages, then a series of cutting devices of varying size and perhaps shape must be employed. This requires the surgeon to repeatedly locate the blockage, guide a first cutting device to it, perform the cutting operation, withdraw the cutting device from the patient, replace it with the next size cutting device in sequence—and then repeat the operation for as many times as is necessary. Repeatedly inserting and removing the cutting devices from the patient is time consuming and increases risk to the patient. In addition, with all cutting devices there is a need to prevent inadvertent cutting into or through healthy arterial walls.

Accordingly, it is an object of the invention to provide an improved atherectomy catheter.

SUMMARY OF THE INVENTION

To this end, an atherectomy catheter includes an incrementally expandable cutter and a torque member attached to the cutter. The cutter is reversibly and incrementally expandable by the surgeon using controls remaining outside of the patient. Preferably, these controls include a cable linked to the cutter and extending through the torque tube to a hand controller. The torque member, which may be a tube, is attached to a motor and a guidewire is axially displaceable through the cutter.

Most desirably, the cable is a braided tube and the cutter includes a plurality of spaced apart blades radially extending from a cutter sleeve. Each blade has a first end integrally joined to the cutter sleeve and a second end joined to the torque member. At its exterior end, i.e. the end remaining outside of the patient, the torque tube is connected to a vacuum source to draw off the material cut away by the cutter. The torque member may optionally have a surface provided with a bioactive material to promote proper healing of the surfaces cut by the cutter.

Also to this end, a method for removing an obstruction in a blood vessel includes the steps of locating the obstruction and guiding an incrementally expandable cutter to the obstruction using a guide wire. The cutter is incrementally expanded and rotated while it is directed to engage the blockage. The cutter may make repeated passes through the blockage removing additional blockage material with each pass.

Other and further objects will appear hereinafter.

BRIEF DESCRIPTION OF THE DRAWINGS

In the drawings, wherein similar reference characters denote similar elements throughout the several views.

DETAILED DESCRIPTION OF THE DRAWINGS

Figure 1:
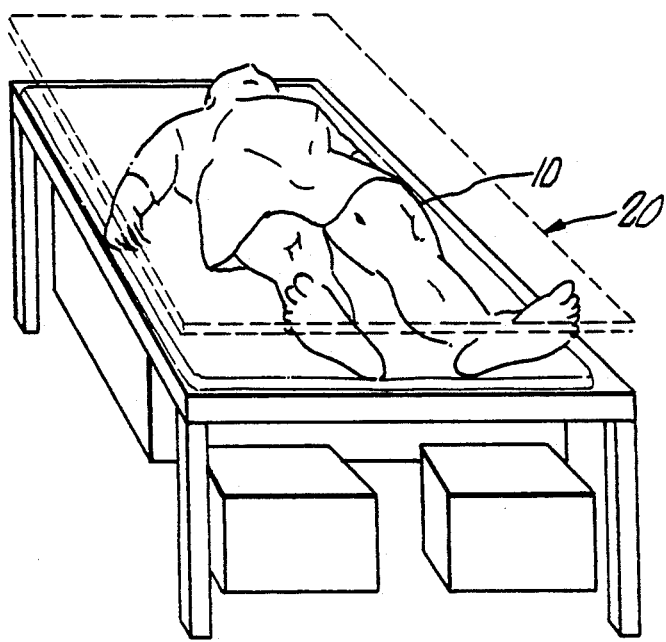
FIG. 1 is a perspective view of a patient and fluoroscope.
Figure 2:
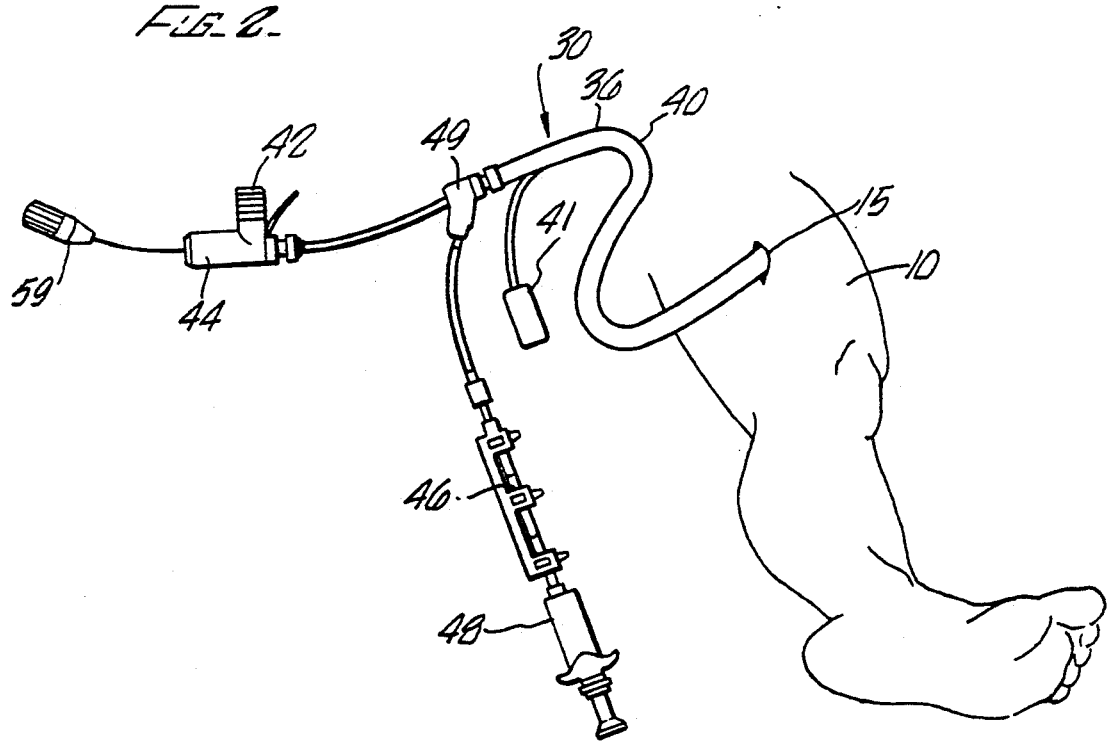
FIG. 2 is a schematic illustration of the exterior end of the atherectomy catheter of the invention.

Turning now to the drawings, as shown in FIGS. 1 and 2, a patient 10 lies on an operating table. A fluoroscope 20 is provided to enable the surgeon to "view" the position of the interior end of the atherectomy catheter 30 after it is inserted into the patient 10.

The exterior end 36 of the catheter 30 includes a torque tube drive motor 44 and vacuum pump 42 connected to a guiding catheter 40. An expander control 46 with a rachet or screw mechanism 48 adjoins to a branch junction 49 connected to the guiding catheter 40.

Figure 3:
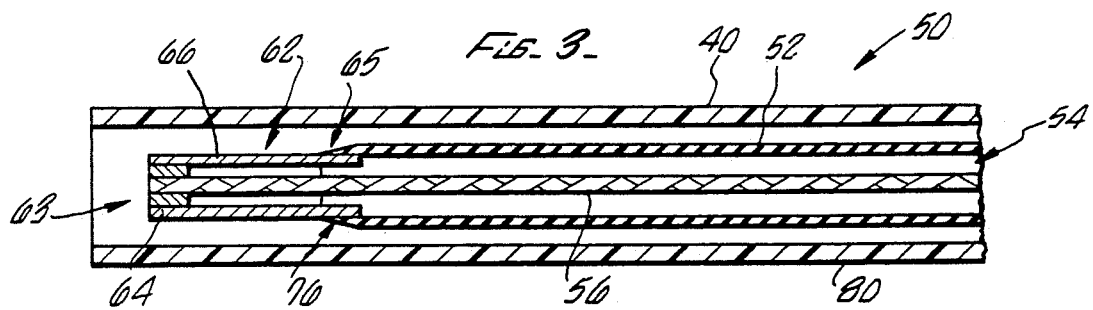
FIG. 3 is a section view fragment of the interior end of the present atherectomy catheter in the fully closed position.
Figure 5:
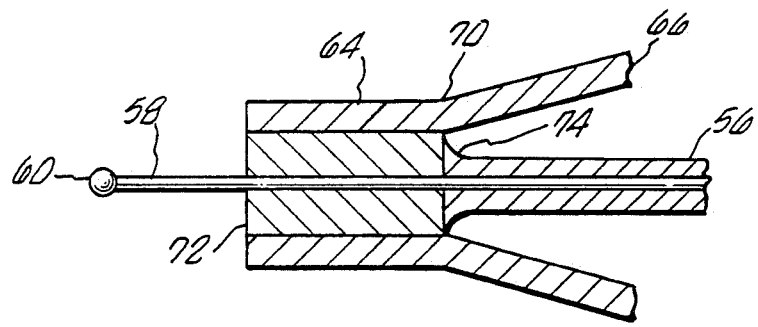
FIG. 5 is an enlarged section view fragment of the front end of the cutter head of the catheter of FIG. 3.
Figure 6:
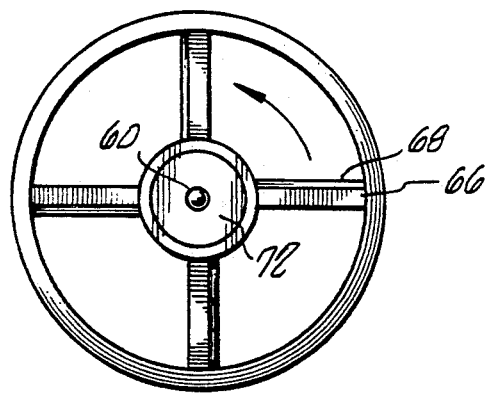
FIG. 6 is a front elevation view thereof.

Referring to FIG. 3, the interior end 50 of the catheter 30 has an expandable cutter head 62 having a plurality of cutter blades 66 joined at the front end 63 of the cutter head 62 to a cutter sleeve 64. As shown in FIG. 6, preferably the cutter head 62 has 4 equally radially spaced apart cutter blades 66 with each blade having a leading or sharpened cutting edge 68. At the back end 65 of the cutter head 62 the cutter blades 66 are attached to a torque tube 52. As shown in FIGS. 3 and 5, a tension cable 56 extends through the torque tube 52 and attaches to the back side of a bushing 72 within the cutter sleeve 64. A guidewire 58 having an end ball 60 extends through a bore in the bushing 72 and through the tension cable 56. The guidewire 58 preferably has as silicone coating to facilitate sliding within the tension cable 56. The cutter head 62 and torque tube 52, as well as the tension cable 56 and guidewire 58 contained therein are axially and slidably positioned within the guiding catheter 40. Similarly, the guidewire 58 is slidably displaceable within the tension cable 56 which itself may also be displaced axially within the torque tube 52.

As shown in FIG. 5, the cutter head 62 has a cutter flexure 70 where each of the cutter blades 66 integrally joins with the cutter sleeve 64. The cutter head 62 may be configured and dimensioned to have a maximum expanded size of up to 8 times the original diameter.

The tension cable 56 is preferably a braided metal cable, with the guide wire 58 and cutter head 62 made of stainless steel or other suitable metal. The torque tube 52 is preferably made of rubber with the guiding catheter 40 made of plastic. The back ends of the cutter blades 66 are bonded to the torque tube 52 at interface 76.

An annulus 54 is formed in between the inside of the torque tube 52 and the tension cable 56. The annulus extends from the cutter head 62 through the torque tube 52 and guiding catheter 40 to the vacuum pump 44. The torque tube 52 similarly extends back through the guiding catheter 40 and is attached to the torque tube drive motor 42. The guidewire 58 and tension cable 56 also extend through the guiding catheter 40 with the tension cable 56 connecting to the expander control 46. The guidewire 58 comes out of the torque tube 52 and is joined to a manipulator 59 (FIG. 2).

In operation, the patient 10 is placed under the fluoroscope 20 and the interior end 50 of the atherectomy catheter 30 is guided through an incision 15 in the patient 10, into a blood vessel. Using the fluoroscope 20 to visualize and determine the position of the interior end 50 of the catheter 30, as well as the location of the targeted blockage, the interior end 50 of the catheter 30 is guided through the blood vessel to the blockage. This is achieved by feeding the guiding catheter 40 through the incision 15 and by guiding or steering the interior end 50 of the catheter 30 by turning the manipulator 59 to maneuver the guide wire 58. While the interior end 50 is guided to the blockage, the cutter head 62 is in the closed or unexpanded position as shown in FIG. 3, with the cutter head 62 fully contained within the guiding catheter 40.

Figure 7:
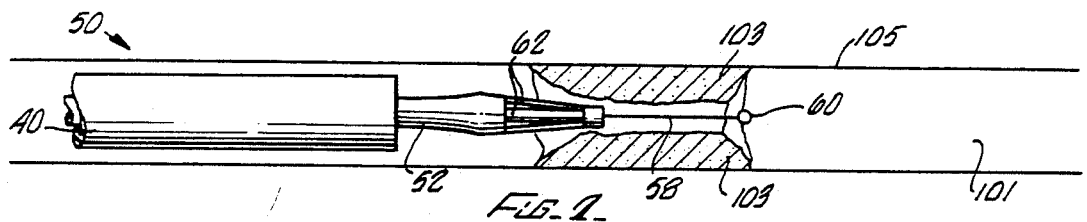
FIG. 7 is a schematic view of the catheter of FIG. 3 with the cutter head partially expanded and beginning the first cutting pass through a blockage.

After the interior end 50 is in position adjacent to a blockage 103 extending from the vessel wall 105, the guiding catheter 40 is pulled back to expose the cutter head 62 as shown in FIGS. 7-11. The guidewire 58 is pushed out of the cutter head 62 using the manipulator 59 so that the end of the guidewire passes all the way through the blockage 103, as shown in FIG. 7. The torque tube drive motor 42 and vacuum pump 44 are turned on causing the cutter head 62 to rotate and causing fluid and material in the annulus 54 to be drawn out.

Figure 4:
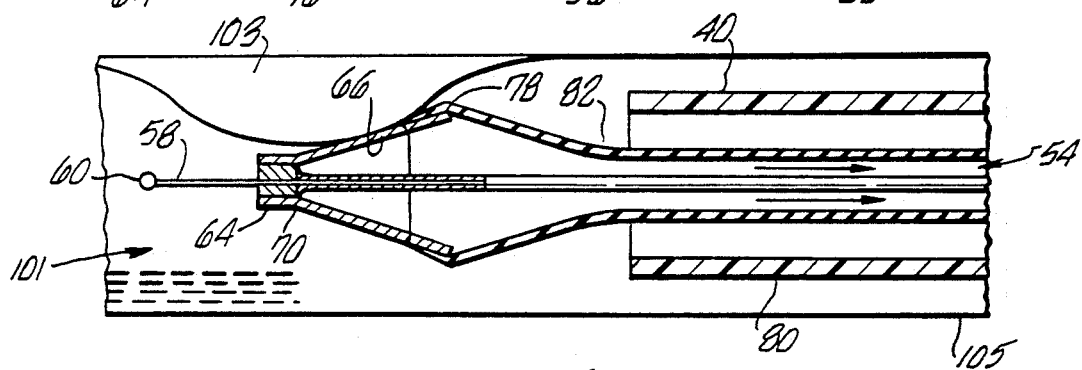
FIG. 4 is a schematically illustrated section view fragment of the catheter of FIG. 3 in a partially open or expanded position within a blood vessel and engaging a blockage.

While viewing the position of the guidewire 58, cutter head 62 and blockage 103, the surgeon then operates the expander control 46 which pulls back on the tension cable 56. This causes the cutter head 62 to expand with the cutter blades 66 flexing outwardly into a generally truncated cone-like configuration. The forward end of the torque tube 52 similarly flexes outwardly, as shown in FIG. 4. The amount of expansion of the cutter head 62 is determined by the amount the tension cable 56 is retracted by the expander control 46. A rachet mechanism 48 facilitates incremental retraction of the tension cable 56 for incremental expansion of the cutter head 62. Alternatively a screw mechanism may be used for an infinitely variable embodiment.

The cutter head is reversibly expandable from a fully closed position where the blades are generally parallel to the cutter axis, to a fully expanded position where the blades form an angle with the cutter axis ranging from approximately 5° to 60°.

Referring to FIGS. 4 and 7-10, the torque tube 52 is pushed forward out of the guiding catheter 40 while it is rotated. The bushing 72 in the cutter head 62 tracks on the guidewire 58 to maintain the cutter head 62 on course through the blockage 103 and to prevent inadvertent cutting into the vessel wall 105. The torque tube 52 is advanced to engage the cutter head 62 into the blockage 103. The guiding catheter 40 does not move. The spinning cutter blades 66 cut or shave off material from the blockage 103 as the cutter head 62 moves forward by pushing the torque tube from the exterior end.

Figure 11:
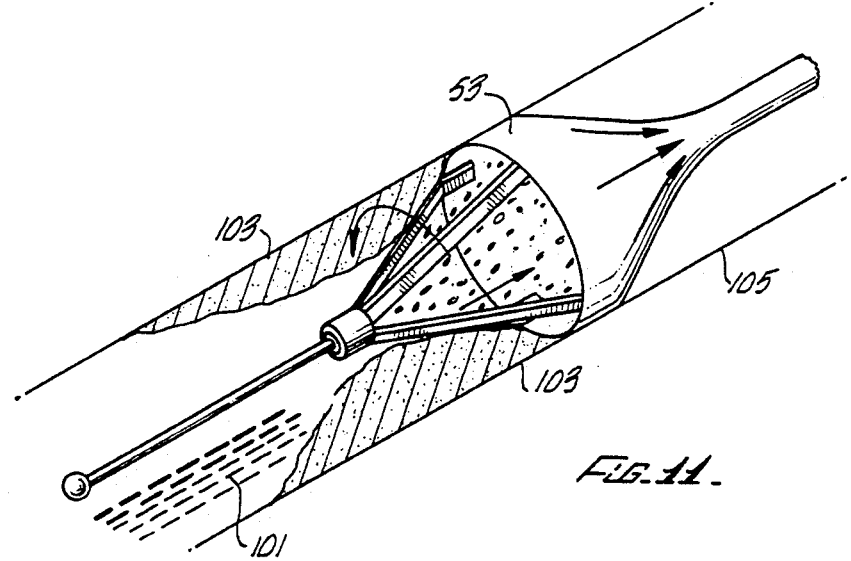
FIG. 11 is a perspective view of the present atherectomy catheter cutting away a blockage.

Referring to FIG. 11, the material cut away from the blockage 103 by the cutter blades 66 is drawn through the cutter head 62 into the annulus 54 and is evacuated from the patient by the vacuum pump 44. A small amount of blood 101 within the vessel is also drawn into the annulus 54 along with the cut away material.

Figure 8:
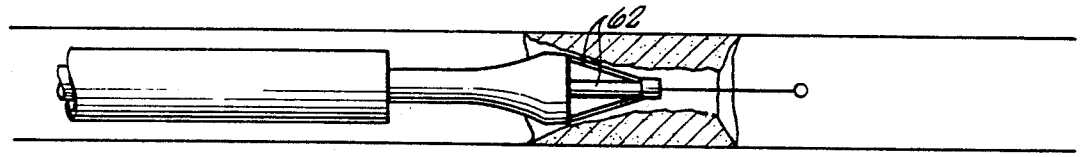
FIG. 8 illustrates the catheter of FIG. 7 with the cutter head further expanded and beginning to make a second pass through the blockage.
Figure 9:
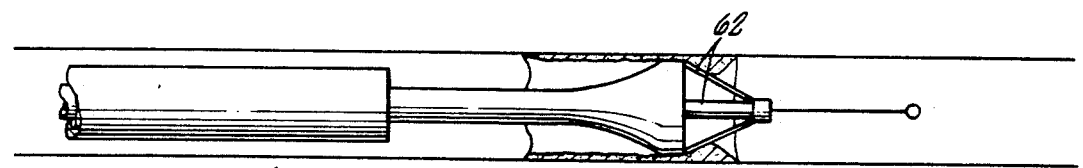
FIG. 9 similarly illustrates preparation for a third pass with the cutter head even more fully expanded.
Figure 10:
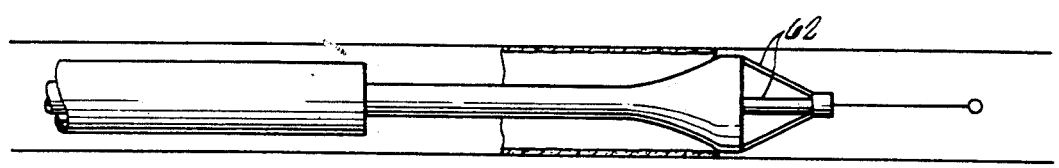
FIG. 10 illustrates the completion of the removal of the blockage with the cutter head substantially fully expanded.

The cutter head 62 is passed entirely through the blockage 103 in the first partially expanded position 62 as shown in FIG. 7. With the guidewire 58 and end ball 60, and guiding catheter 40 remaining substantially in position, the torque tube 52 is withdrawn so that the cutter head 62 is pulled back through the blockage 103 in preparation for a second pass. Using the expander control 46, the tension cable 56 is retracted by a second increment thereby causing the cutter head 62 to expand to a second position as shown in FIG. 8. The cutter head, now in the second expanded position, is then again passed through the blockage 103. The technique is repeated as shown in FIGS. 9 and 10, with the cutter head 62 being incrementally expanded with each consecutive pass through the blockage 103. Depending upon the nature of the blockage 103, a single pass may be sufficient or multiple passes may be required. Since the guiding catheter 40 remains in position through the repeated passes of the cutter head 62, the risk of damage to blood vessels by movement of the guiding catheter 40 is minimized, and the guiding catheter 40 need only be guided into position once to remove the blockage 103.

A bio-active surface 53 having biologically active compounds such as epidermal growth factor (EGF); transforming growth factor (TGF), alpha and beta; platelet derived growth factor (PDGF); fibroblast growth factor (FGF); and insulin-like growth factor (IGF), bound to it is provided on the leading cylindrical edge of the torque tube 52. As the bio-active surface 53 contacts the freshly cut tissues of the blockage 103, the bioactive compounds on the bio-active surface 53 are brought into contact with the tissues to promote healing or inhibit recurrent growth. The bio-active material may be covalently bonded to the torque tube 52.

After the blockage has been substantially entirely cut away, as shown in FIG. 10, the vacuum pump 44 and torque tube motor 42 are turned off, and the tension cable 56 is released or pushed forward by the expander control 46 causing the cutter head 62 to contract to the original closed configuration shown in FIG. 3. The torque tube 52 is withdraw into the guiding catheter 40 and the guidewire 58 is similarly pulled back into the tension cable 56 with the interior end 50 of the atherectomy catheter 30 in the position as shown in FIG. 3. The guiding catheter 40 containing the cutter head 62 is then withdrawn from the patient.

An application lumen or tube 41 may be attached to the guiding catheter 40 to facilitate providing a biologically active compound, such as EGF, TGF, PDGF, FGF or IGF directly to the intervention site. The biologically active compound in solution, is injected or otherwise pumped into the application lumen 41 which joins to and leads into the guiding catheter 40. The solution flows through the guiding catheter 40 to the interior end 50 where it is released immediately adjacent to the intervention site or the tissue cut by the atherectomy catheter. Since the biologically active compound is released virtually directly onto the intervention site, therapeutic levels of the compounds can be reached with the administration of an extremely small quantity of the compound.

Thus, although several embodiments have been shown and described, it will be apparent to those skilled in the art that may other embodiments and variations are possible without departing from the spirit and scope of the invention.

What is claimed is:

1. An atherectomy catheter comprising:
   a central guidewire;
   a cutter sleeve slidably and rotatably positioned around the guidewire;
   a variably expandable cutter having a plurality of substantially straight blades having front and back ends, with the front end of each blade attached to the cutter sleeve through a flexure;
   a torque tube around the guidewire having a leading end attached around and overlying the back ends of the blades, the cutter variably expandable from a closed position wherein the blades are generally straight and parallel to each other to an open position wherein the blades are generally straight and extend away from each other from their front ends to their back ends, the leading end of the torque tube having a diameter larger than any diameter traced by the blades as the cutter turns; and
   a pullback cable around the guidewire and within the torque tube and attached to the cutter sleeve.

2. The atherectomy catheter of claim 1 further comprising a guiding catheter substantially enclosing the torque tube, with the torque tube rotatable and axially displaceable within the guiding catheter.

3. The atherectomy catheter of claim 2 further comprising vacuum means attached to the torque tube.

4. The atherectomy catheter of claim 1 further comprising a bio-active material covalently bonded to a surface on the torque tube adjacent the cutter.

5. The atherectomy catheter of claim 1 further comprising a hand controller connected to the pullback cable.

6. The atherectomy catheter of claim 5 wherein the hand controller comprises a ratchet device.

7. The atherectomy catheter of claim 1 further comprising a manipulator attached to the guidewire.

8. The atherectomy catheter of claim 1 further comprising means for rotating the torque tube.

9. The atherectomy catheter of claim 1 wherein the back ends of the blades are reversibly expandable radially outwardly from the cutter sleeve from a fully closed position wherein the blades are substantially parallel to each other to a fully open position wherein the blades form an angle with the guidewire of up to about 60°.

* * * * *